United States Patent [19]

Chia et al.

[11] Patent Number: 5,354,676
[45] Date of Patent: Oct. 11, 1994

[54] RECOMBINANT MODIFIED THERMOSTABLE NAD-DEPENDENT DEHYDROGENASES AND PROCESS FOR THEIR PRODUCTION

[75] Inventors: William N. Chia, Singapore, Singapore; Anthony R. Clarke, Bristol, England; Joseph J. Holbrook, Bath, England; Helen M. Wilks, Bristol, England; Anthony Atkinson, Wiltshire, England

[73] Assignees: The University of Bristol; Public Health Laboratory Service Board, both of England

[21] Appl. No.: 768,881
[22] PCT Filed: Mar. 7, 1990
[86] PCT No.: PCT/GB90/00345
 § 371 Date: Oct. 24, 1991
 § 102(e) Date: Oct. 24, 1991
[87] PCT Pub. No.: WO90/10702
 PCT Pub. Date: Sep. 20, 1990

[30] Foreign Application Priority Data

Mar. 8, 1989 [GB] United Kingdom .............. 8905269.0

[51] Int. Cl.$^5$ ............................................. C12N 9/04
[52] U.S. Cl. ..................................... 435/190; 930/240
[58] Field of Search ................................ 935/190, 67.2

[56] References Cited

PUBLICATIONS

Grou et al., J. Mol. Biol. 151, 289–307 (1981).
Clarke et al., Nature, vol. 324, pp. 699–702 (1986).
Wigley et al., J. Mol. Biol. vol. 223 pp. 317–335 (1992).
Murphey et al., J. Biol. Chem. vol. 242(7) pp. 1560–1565 (1967).
Wilks et al., Science, vol. 242 pp. 1541–1544 (1988).
Hart et al., Biochem. Biophys. Res. Comm. vol. 146 pp. 346–353 (1987).
Wigley et al., Biochim Biophys Acta vol. 916 pp. 145–148 (1987).
Imanaka et al., Nature vol. 324 pp. 695–697 (1986).

*Primary Examiner*—Robert A. Wax
*Assistant Examiner*—David B. Schmickel
*Attorney, Agent, or Firm*—Kirschstein, Ottinger, Israel & Schiffmiller

[57] ABSTRACT

A recombinant thermophilic NAD-dependent dehydrogenase having a hydrophobic amino acid at position 104 and/or 102. The enzymes are effective in catalysing the dehydrogenation of homologues of pyruvic acid of formula $CnH_{2n+1}COCOOH$, wherein n is > 1, to homologues of lactic acid of formula $CH_nH_{2n+1}CHOH$-COOH, wherein n is > 1.

2 Claims, 5 Drawing Sheets

FIG. 1

```
                          CATCCGCTATATTAAGCTGGGTGCTGCCGTTTGCCTTTATCCAGCTT
     -35(M)                                      20          40 -35(I)
                                                    -10(IV)
CGTATTTCTCCATAAGCAGGAATGGTTATGCCGTTTTTGACCCGGTGTCCGCCATGTTTTT
60       -10(I)              80                    100 -35(II)         120       -10(II)

CATCATCCGCCGTGATGCTCTGGAGCTCTGGGTCAGGAGGTACCCGGGGAGCTGAGTGCTCC
        140                         160            A      180

CGTTGTTTGCCCGGGCTCTCATGAAATGGACACAAACAATAGTCAAACAATCGCCACAATCGCCATGC
200            220 -35(III)              240    10(III)              260    SphI
     A'                                          A                          B

ATGCGGGTGCCCTTTCGCGTAAAATATTTATGAAAGTGTTCGCATTATATTGAGGAGGATGAATGCA
         280                           300              320   S.D.    B

Met Lys Asn Asn Gly Gly Ala Arg Val Val Ile Gly Ala Gly Phe Val Gly Ala
ATG AAA AAC AAC GGT GGA GCC CGA GTC ATC GGC GCC GGG TTT GTC GGC GCC
340                              360                           380

Ser Tyr Val Phe Ala Leu Met Asn Gln Gly Ile Ala Asp Glu Ile Val Leu Ile Asp
AGT TAT GTG TTT GCC TTA ATG AAT CAA GGG ATT GCC GAT GAG ATC GTC ATC GAT
400                              420                           440

Ala Asn Glu Ser Lys Ala Ile Gly Asp Ala Met Asp Phe Asn His Gly Lys Val Phe
GCG AAT GAA AGC AAG GCC ATA GGC GAT GCG ATG GAC TTC AAC CAT GGG AAA GTA TTT
460                              480                           500

Ala Pro Lys Pro Val Asp Ile Trp His Gly Asp Tyr Asp Asp Cys Arg Asp Ala Asp
GCG CCG AAG CCG GTT GAC ATT TGG CAC GGC GAT TAC GAT GAT TGC CGC GAT GCC GAT
520                              540                           560

Leu Val Val Ile Cys Ala Gly Ala Asn Gln Lys Pro Gly Glu Thr Arg Leu Asp Leu
TTG GTT GTC ATT TGC GCC GGC GCC AAC CAA AAA CCG GGC GAG ACG CGG CTT GAT CTT
580                              600                           620
```

FIG. 2

```
Val Asp Lys Asn Ile Ala Ile Phe Arg Ser Ile Val Glu Ser Val Met Ala Ser Gly
GTG GAC AAA AAG ATT GCC ATT TTC CGC TCG ATC GTT GAG TCG GTC ATG GCA TCC GGA
                    640                     660                     680

Phe Gln Gly Leu Phe Leu Val Ala Thr Asn Pro Val Asp Ile Leu Thr Tyr Ala Thr
TTT CAA GGA CTG TTT CTC GTC GCC ACC AAT CCG GTC GAC ATT TTA ACG TAC GCG ACG
                    700                     720 SalI

Trp Lys Phe Ser Gly Leu Pro His Glu Arg Val Ile Gly Ser Gly Thr Ile Leu Asp
TGG AAA TTC AGC GGC CTG CCG CAT GAG CGG GTG ATC GGT TCG GGA ACG ATT TTA GAT
                    740                     760                     780

Thr Ala Arg Phe Arg Phe Leu Gly Glu Tyr Phe Ser Val Ala Pro Gln Asn Val
ACG GCG CGG TTC CGC TTT TTG GGC GAG TAT TTC TCT GTC GCT CCG CAA AAT GTT
                    800                     820                     840

His Ala Tyr Ile Ile Gly Asp Thr Glu Leu Pro Val Trp Ser Gln Ala
CAT GCC TAT ATT ATT GGG GAA CAC GAC ACT GAA CTC CCG GTC TGG AGC CAG GCT
                    860                     880                     900

Tyr Ile Gly Val Met Pro Ile Arg Ile Phe Val Asn Val Glu Leu Val Glu Ser Lys Gly Glu Glu Ala Gln
TAT ATC GGC GTG ATG CCG ATC CGC ATT TTT GTC AAT GTG CTG GTC GAG TCC AAA GGG GAA GAA GCG CAA
                    920                     940                     960

Lys Asp Leu Glu Arg Ile Glu Arg Ile Glu Arg Ile Glu
AAA GAT CTC GAG CGC ATT GAG
    BglII   XhoI    980

Lys Gly Ala Thr Tyr Tyr Gly Ile Ala Met Gly Leu Val Glu Arg Ala
AAA GGA GCG ACG TAC TAC GGG ATT GCC ATG GGG CTT GCC GTG CGC GCC
                    1040                    1060                    1080

Ile Leu His Asn Glu Asn Ala Ile Leu Leu Thr Val Ser Ala Tyr Leu Asp Gly Leu Tyr
ATT TTG CAT AAC GAA AAC GCT ATT TTG ACC GTA TCA GCC TAC CTC GAT GGC CTA TAT
                    1100                    1120
```

FIG. 3

```
Gly Glu Arg Asp Val Tyr Ile Gly Val Pro Ala Val Ile Asn Arg Asn Gly Ile Arg
GGG GAG CGC GAC GTC TAC ATC GGA GTG CCG GCT GTC ATT AAC CGC AAT GGC ATC CGC
                    1140                1160                1180

Glu Val Ile Glu Ile Glu Leu Asn Asp Glu Lys Asn Arg Phe His His Ser Ala
GAG GTG ATC GAA ATT GAA TTG AAT GAT GAC GAA AAA AAT CGA TTC CAT CAT AGC GCA
              1200                1220                1240

Ala Thr Leu Lys Ser Val Leu Ala Arg Ala Phe Thr Arg •
GCT ACA TTA AAA AGC GTG CTA GCC CGT GCT TTT ACG CGA TGAGGCAACAACGAAAGTT
              1260                1280                        1300

GTGCCGACAGTCTTTCTCGTCCAAACAGGGGATGTATGGCTCTGAGGGC
              1320                1340                1360
```

Figure 1:
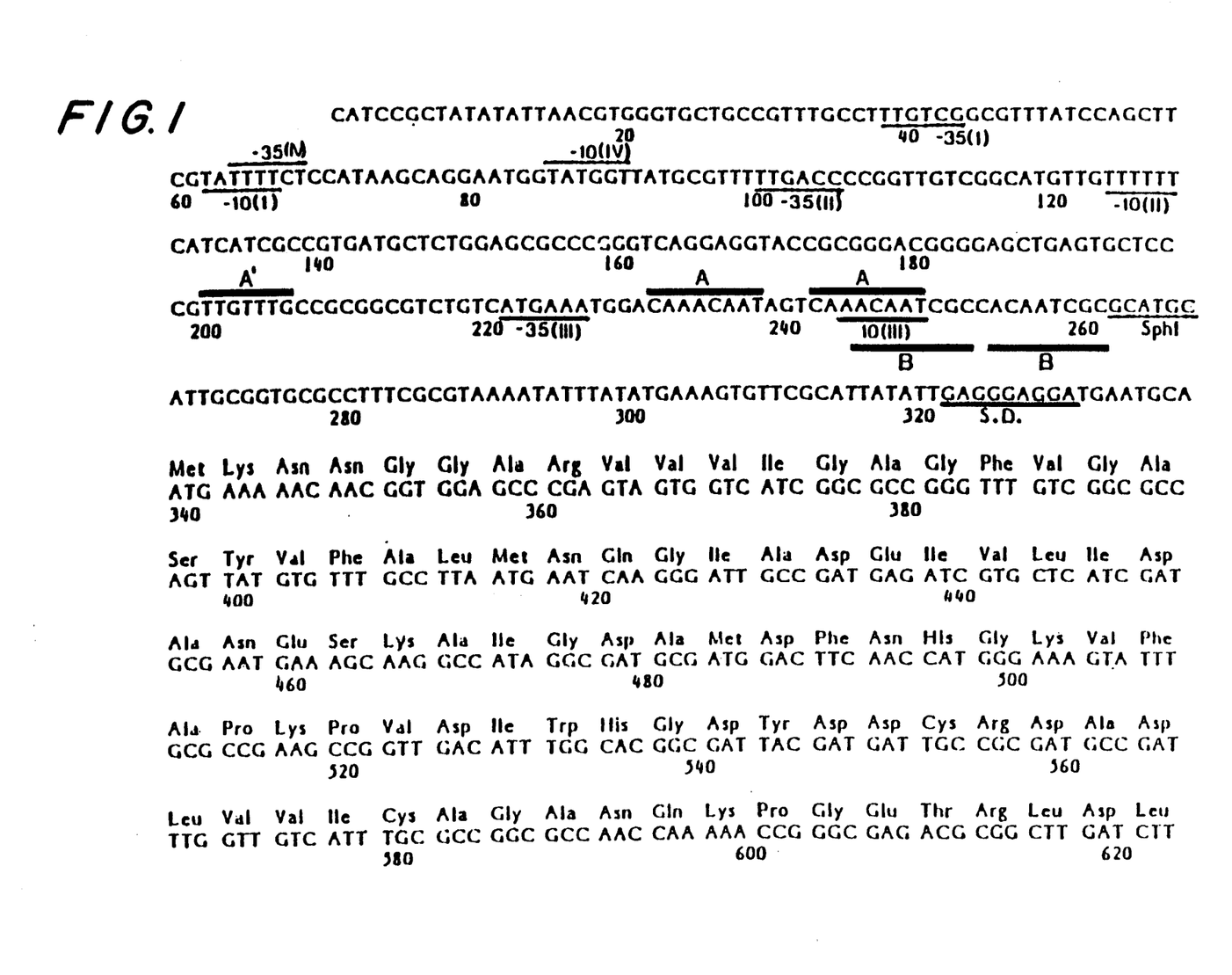
Figure 2:
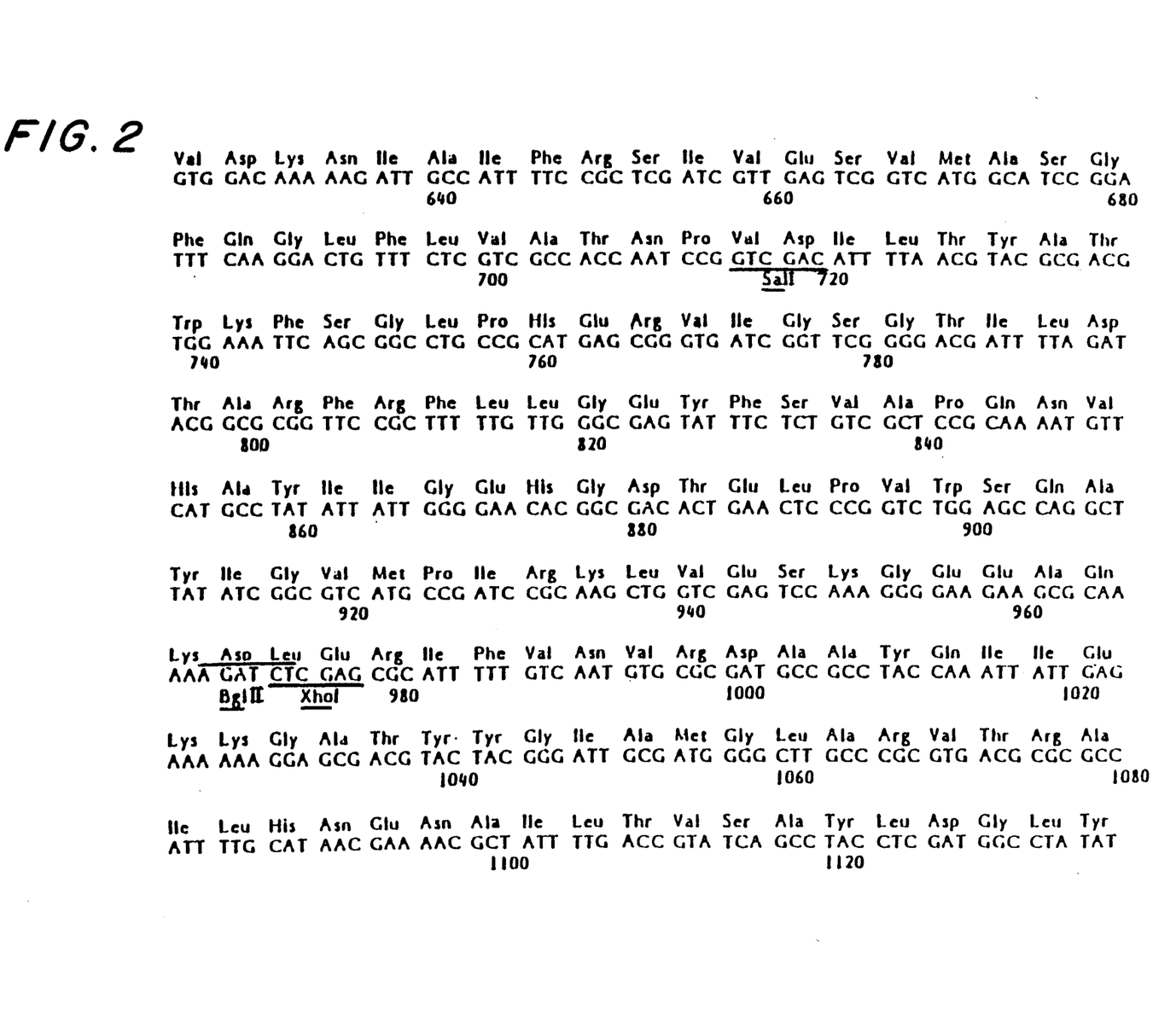
Figure 3:
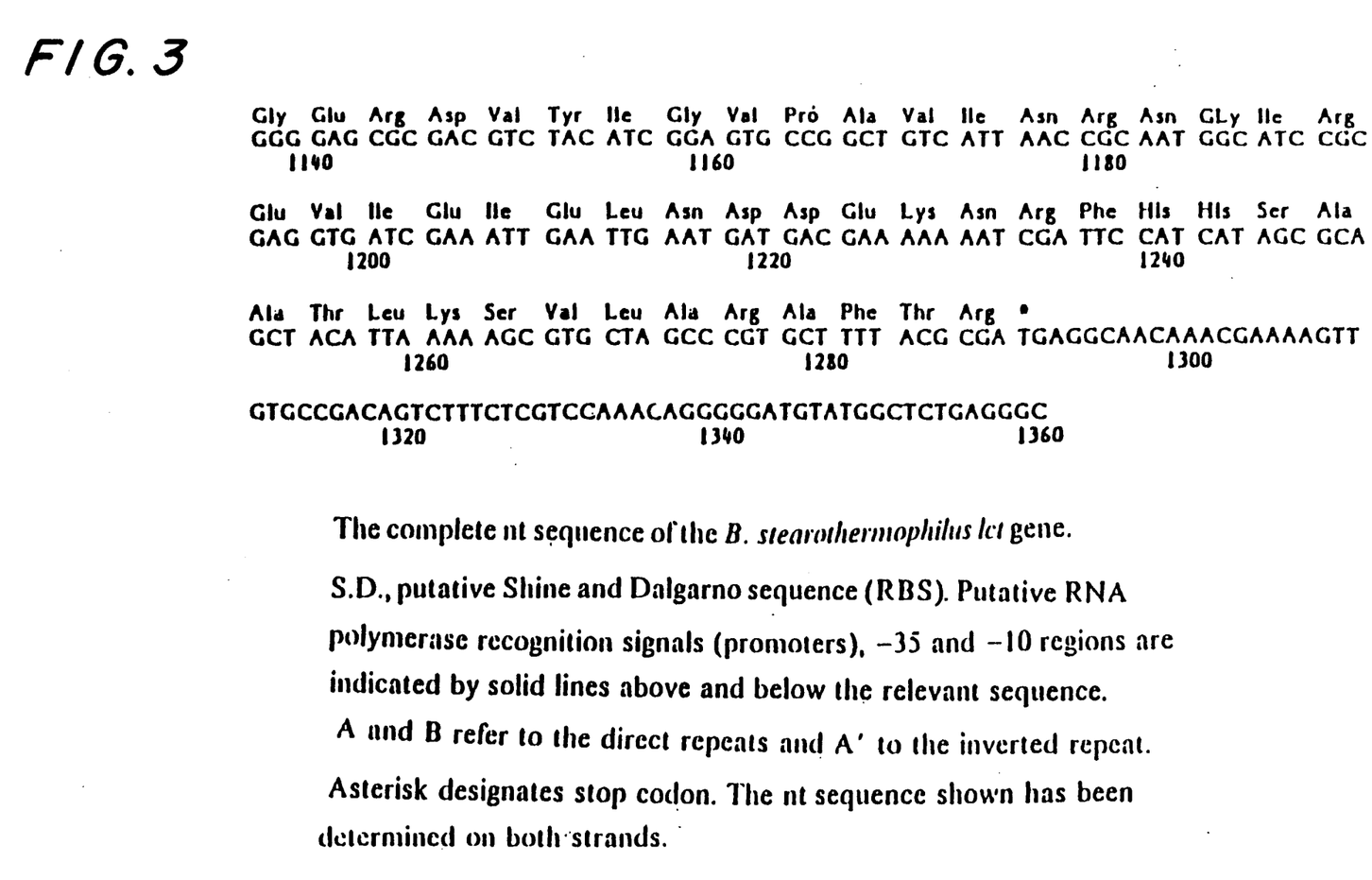
Figure 4:
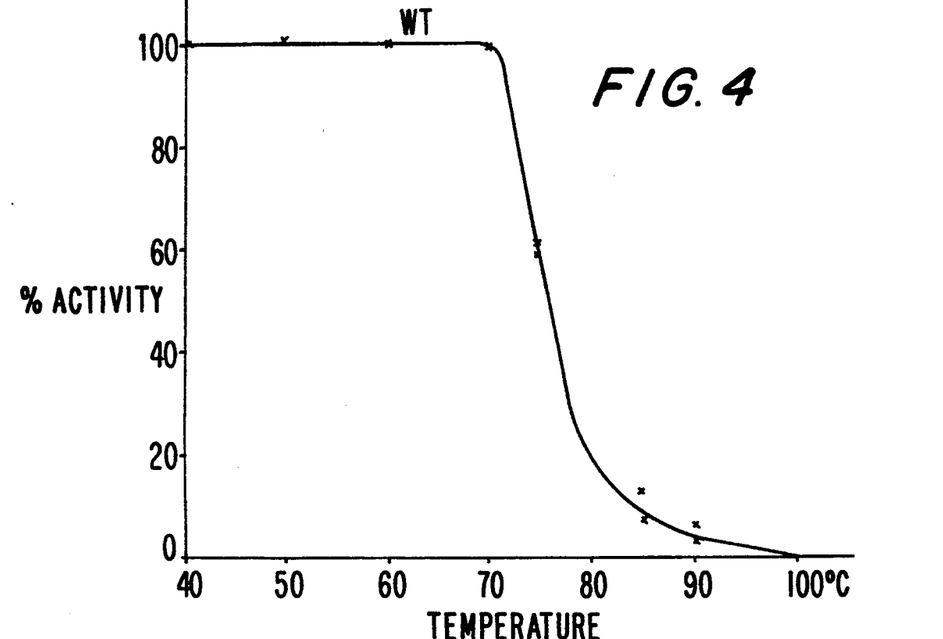
Figure 5:
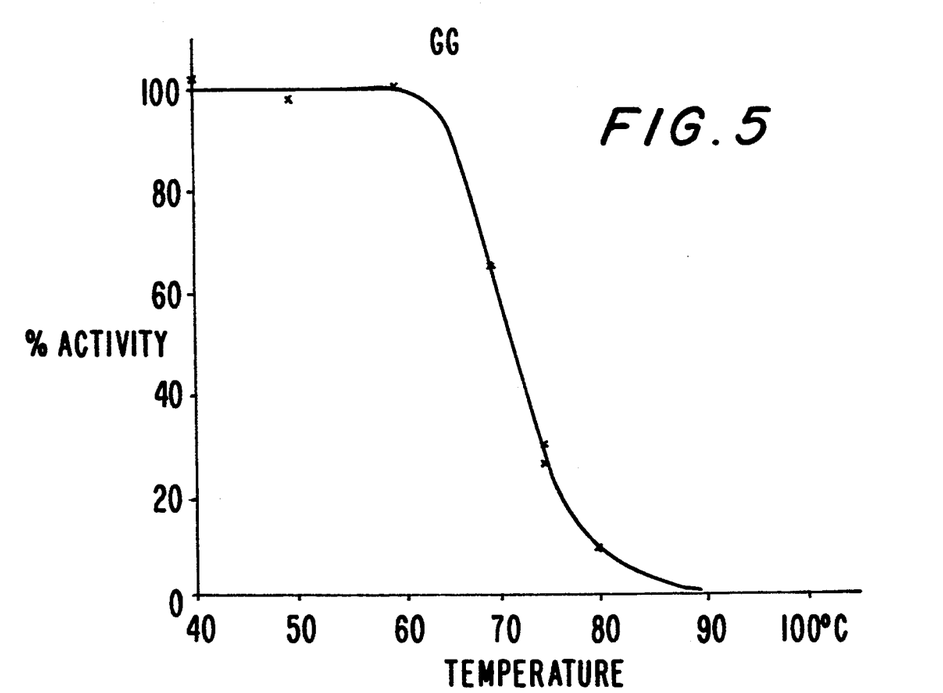
Figure 6:
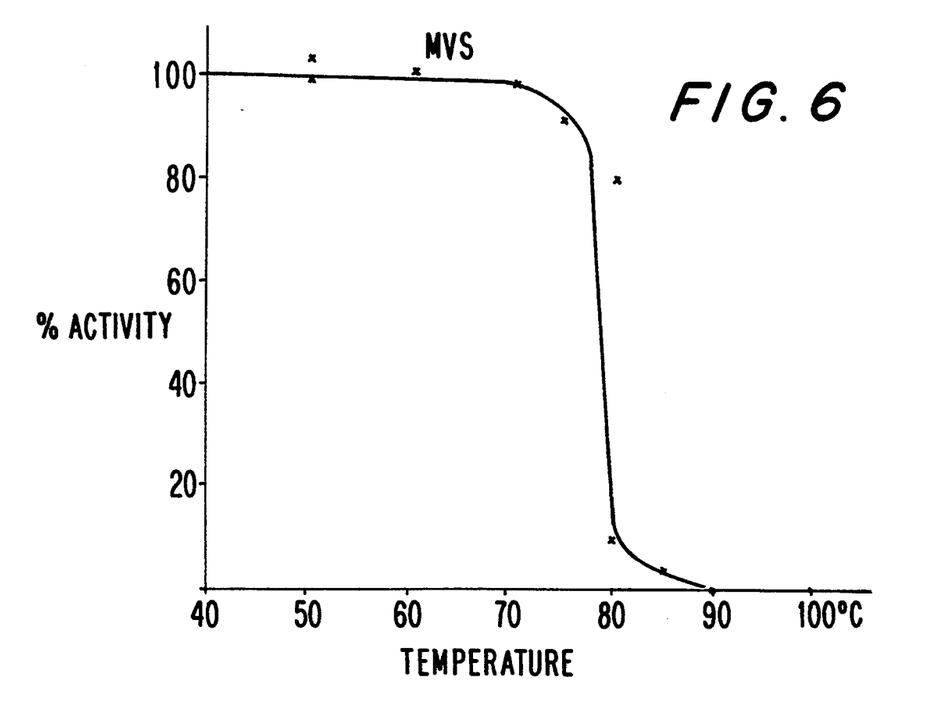
Figure 7:
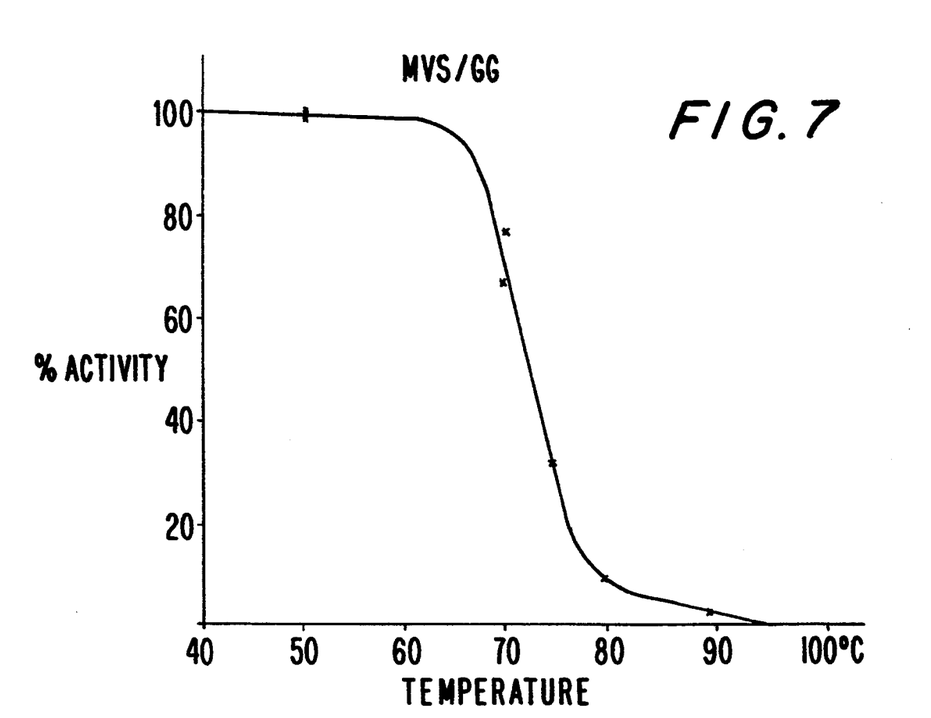

The complete nt sequence of the *B. stearothermophilus lct* gene.

S.D., putative Shine and Dalgarno sequence (RBS). Putative RNA polymerase recognition signals (promoters), −35 and −10 regions are indicated by solid lines above and below the relevant sequence.

A and B refer to the direct repeats and A' to the inverted repeat.

Asterisk designates stop codon. The nt sequence shown has been determined on both strands.

RECOMBINANT MODIFIED THERMOSTABLE NAD-DEPENDENT DEHYDROGENASES AND PROCESS FOR THEIR PRODUCTION

This invention relates to novel modified NAD-dependent dehydrogenases.

Proteins are extremely effective as catalysts for chemical conversions end have evolved to be highly selective. One possibility now emerging from the ability to chemically synthesise genes is the design end construction of proteins with properties not available in nature.

NAD-dependent dehydrogenases are frequently used in assay systems end in stereospecific syntheses of organic compounds. These enzymes catalyse both the hydrogenation of α-keto acids to α-hydroxy acids and the oxidation (dehydrogenation) of α-hydroxy acids to give α-karo acids. The native NAD-dependent dehydrogenase obtained from *Bacillus stearothermophilus* has activity as a lactate dehydrogenase, but has little activity as a dehydrogenase for other substrates. A feature of this particular enzyme is that it is highly thermophilic, i.e. it has a half-life of five minutes at 90° C.

There is a need for modified NAD-dependent dehydrogenases, particularly ones which are thermally stable, and which have enzymic activity on selected substrates.

Thermophilic enzymes which have that property are more desirable than mesophilic ones for use in the production of long chain S-lactates which have value as chiral intermediates in pharmaceutical synthesis. Chiral lactates are useful intermediates for the synthesis of both off-patent generic and potential new pharmaceutical products. Many such compounds are currently marketed as Pacemates. However the fear of US and eventually European legislation in favour of single compound drags, and their higher audistoic ratios has caused an increase in the proportion of enantiomerically pure compounds being submitted for screening by Committee on Safety of Medicines. There is thus commercial advantage in an enzyme system which can be engineered to synthesize such chiral intermediates.

In GB 8806358 we identified residues contributing to the substrate recognition site of NAD-dependent dehydrogenases and showed that the site is present, at least in part, in a particular amino acid sequence. We further described certain modifications to that sequence which resulted in the formation of NAD-dependent dehydrogenases having, inter alia, different substrate specificities and other commercially desirable properties. Specifically, we have demonstrated that it is possible to alter the substrate specificity of the nicotinamide adenine dinucleotide (NAD)-dependent L-lactate dehydrogenase (LDH) from *B. stearothermophilus* from lactate to malate, producing a highly specific catalyst for the new substrate.

To alter or broaden the specificity of an enzyme it is necessary to have a detailed understanding of the mechanism so that the "central" chemistry can be retained. In the case of enzymes with small substrates, the catalytic and specificity sites are necessarily close together, making it difficult to alter substrate specificity without affecting catalysis.

We have now developed a mutation strategy which has enabled the production of NAD-dependent dehydrogenases which are thermophilic and which have a particularly desirable substrate specificity.

Specifically the novel enzymes of the invention are effective in catalysing the dehydrogenation of homologues of pyruvic acid of formula $C_nH_{2n+1}COCOOH$ wherein n is $>1$, to homologues of lactic acid of formula $CH_nH_{2n+1}CHOHCOOH$ wherein n is $>1$. Examples of resiues $C_nH_{2n+1}$ include straight and branched chain alkyl rsidues having 2 to 6 carbon atoms, including ethyl, n-propyl, iso-propyl, n-butyl, iso-butyl end sec-butyl.

The wild type lactate dehydrogenases have very poor rates of reaction with long, branched α-karo acids and the corresponding α-hydroxy acids. The new enzymes we have synthesized have much more desirable properties with the higher homologues referred to above.

Such enzymes are of particular value in the field of, for example, synthetic chemistry where it is desired to convert a keto compound stereospecifically to a corresponding secondary alcohol. The production of individual optical isomers (chiral forms) of secondary alcohols is especially valuable in the manufacture of optical isomers of pharmaceuticals end drug intermediates. The feature of thermophilicity is valuable because it enables the enzymic reactions to be carried out at relatively high temperatures where a rate advantage exists end the enzymes are inherently more stable.

For example the construction MVS/GG described below is much faster than wild-type lactate dehydrogenase in the reduction of alphaketo isocaproate (KIC) by a ratio of 18.5:0.33 i.e. about 50 times better.

In the field of NAD-dependent dehydrogenases, a conventional numbering system has evolved, which was originally based on an sequence of dog-fish muscle lactate dehydrogenase. This numbering system numbers amino acids in ascending order in a direction extending from the N-terminus. A discussion of this numbering system is to be found in a paper by Eventoff, W. et al, (1977) Proc. Natl. Acad. Sci. (USA), Vol. 74, pp. 2677–2681.

In this conventional numbering system, amino acid residues in a given polypeptide are not necessarily numbered consecutively from the N-terminus starting with one. Nonetheless there are so-called "essential" end "conserved" amino acids which are always given the same numbers irrespective of the locations at which they appear (counted from the N-terminus). Examples are the two highly conserved glycine residues at positions 30 and 33, the tyrosine at position 85, the argintne at position 109, the serine at position 164 end the aspartic acid at position 168.

In a given polypeptide which is a NAD-dependent dehydrogenase (but which is not necessarily a naturally evolved enzyme) there are regions of sequence which are homologous with the amino acid sequence of the conventional numbering system end which enable an alignment of amino acids to be achieved.

Such an alignment of amino acid sequences is shown in Table 1 for three NAD-dependent lactate dehydrogenases: the H4 isoenzyme of pig, the testis isoenzyme of man end the *B. stearothermophilus* enzyme.

Using similar alignments of their amino acid sequences, "essential" and "conserved" amino acids of other NAD dependent α-karo acid dehydrogenases may be identified and the numbering correlated with that of the conventional numbering system.

In Table 1, the symbols "—" do not signify breaks in the contiguous polypeptide chain; instead they are conventional representations of discontinuities of numbering which allow alignment with sequences of other enzymes to give maximum homology.

TABLE 1-continued

| | | | 5 | | | | | | 0 | | | | 5 | | | | 0 | | | | 5 | | | | 0 | | | | 5 | | | | 9 | |
|---|---|---|---|---|---|---|---|---|---|---|---|---|---|---|---|---|---|---|---|---|---|---|---|---|---|---|---|---|---|---|---|---|---|---|
| PIG H | S | T | M | V | Q | G | — | — | — | M | Y | G | I | E | N | V | F | L | L | P | C | V | L | N | A | R | G | L | T | S | | | | |
| MAN X | S | T | M | V | K | G | — | — | — | L | Y | G | I | K | E | L | F | L | S | I | P | C | V | G | R | N | G | V | S | D | | | | |
| B STEAR | S | A | Y | — | L | G | — | — | — | L | — | — | E | R | D | — | V | Y | I | G | V | A | I | N | R | — | I | R | E | | 130 | | 135 | |

| | | | | | | | | | | | | | | | | 5 | | | | 3 0 | | | 3 2 5 | | | | 3 3 0 | | | | 3 3 5 | | |
|---|---|---|---|---|---|---|---|---|---|---|---|---|---|---|---|---|---|---|---|---|---|---|---|---|---|---|---|---|---|---|---|---|---|
| PIG H | — | — | V | I | N | Q | K | L | K | D | D | E | V | A | Q | L | S | A | D | T | L | W | G | I | Q | K | D | L | K | A | B | D | L | — | F | R |
| MAN X | — | — | V | V | K | I | D | B | E | E | L | Y | A | L | L | E | S | A | E | T | L | L | W | N | I | Q | K | N | L | I | A | K | L | I | T | R |
| B STEAR | — | — | I | E | I | L | L | N | D | E | K | N | H | H | S | A | A | T | A | L | K | S | V | L | A | R | A | F | T | R |

REFERENCES

MAN X: Expression cloning of human testis-specific lactate
dehydrogenase cDNA.
Millan, J. L., Driscoll, C. E. and Goldberg E.
Unpublished sequence from cDNA (October 1986).
B STEAR: The DNA sequence of the thermophilic lactate
dehydrogenase from *Bacillus stearothermophilus.*
Barstow, D., Clarke, A. R., Wigley, D., Holbrook, J. J. and
Atkinson, T. Gene 46 (1986) 47–55

Within the conventional numbering system, we have identified short sequences which can be correlated with specific structural elements in the folded polypeptide and which may have specific functional properties. For example, they may form the catalytic pathway, the substrate recognition site or the activator site.

The substrate recognition site is carried in part by a mobile loop of polypeptide chain, conventionally numbered 98 to 110. This sequence is continuous but traditionally omits a residue 103.

The sequence can be identified by the following residues in positions 106–110:

|           |     |
|-----------|-----|
| Gly       | 106 |
| Glu       | 107 |
| Ser or Thr| 108 |
| Arg       | 109 |
| Leu       | 110 |

According to one aspect of the present invention, there is provided a recombinant thermophilic NAD-dependent dehydrogenase having a hydrophobic amino acid at at least one of positions 102 and 104. Preferably, said hydrophobic amino acid is selected from methionine, valine, isoleucine and leucine.

As used herein in accordance with the conventional numbering system of NAD dependent dehydrogenases, "position 102" means the position in the conventional numbering system which is six residues to the N-terminal side of the highly conserved arginine at position 109. Similarly, "position 104" means the position in the conventional numbering system which is five residues to the N-terminal side of the highly conserved arginine at position 109.

This is shown in the following representation:

$$\ldots aa_{102}.aa_{104}.aa_{105}.aa_{107}.aa_{108}.Arg \ldots$$

(It is to be noted that position 103 is conventionally absent and no amino acid numbered "103" appears in the above representation).

For reasons explained in greater detail below, the recombinant thermophilic NAD-dependent dehydrogenases according to the invention desirably have a hydrophobic amino acid both at position 102 and at position 104.

Most preferably the hydrophobic amino acid at position 102 is methionine and the hydrophobic amino acid at position 104 is valine.

It is further desirable for the recombinant thermophilic NAD-dependent dehydrogenases according to the invention to have a hydrophilic amino acid at position 105, for example a serine residue.

According to a further aspect of the invention, there are provided recombinant thermophilic NAD-dependent dehydrogenases having in the region extending from positions 234 to 237 at least one amino acid capable of destabilising α-helices. Examples of such amino acids include glycine and proline residues. Preferably a glycine residue is provided at at least one of positions 235 and 236. Most preferably a glycine residue is provided at at both of positions 235 and 236.

According to a particularly preferred aspect of the invention, both of the features referred to above are incorporated, i.e. the presence of a hydrophobic amino acid at at least one (and preferably both) of positions 102 and 104 and the presence in the region extending from positions to 237 at least one amino acid capable of destabilising α-helices.

Recombinant thermophilic NAD-dependent dehydrogenase according to the invention have been found to possess a higher catalytic activity for homologues of lactic acid of formula $C_nH_{2n+1}CHOHCOOH$ wherein n is $>1$ as substrate, than for lactate. The dehydrogenases according to the invention are accordingly useful in catalysing dehydrogenation reactions of α-karo acids such as α-keto burytic acid. [$CH_3.CH_2.CO.COOH$], α-karo valetic acid [$CH_3(CH_2)_2COCOOH$], α-keto caproic acid [$CH_3(CH_2)_3CO.COOH$], α-karo isovaleric acid [($CH_3$)$_2$CHCOCOOH)] and α-karo isocaproic acid [($CH_3$)$_2$CHCH$_2$COCOOH].

The recombinant NAD-dependent dehydrogenase according to the invention are, as indicated. thermophilic. As such, they are particularly useful as catalytic reagents for industrial purposes as they are stable (thus increasing their useful life) and further they can be used at relatively high reaction temperatures without their decomposition rate becoming excessively high. Consequently they may be used at relatively high temperatures, at which the rate of the required reactions are increased. As used herein, the term "thermophilic" refers to an enzyme which is stable for 20 minutes in 100mM triethanolamine chloride at pH 6 at a temperature $>50°$ C., particularly one which is stable for 20 minutes in 100 mM triethanolsmine chloride at pH 6 at a temperature $>60°$ C.

The recombinant thermophilic dehydrogenese enzymes of the invention may conveniently possess a substantial amino acid homology with the wild type lactate dehydrogenase of *B. stearothermophilus* which is itself thermophilic. Thus according to a further aspect of the invention, them is provided a recombinant thermophilic NAD-dependent dehydrogensse consisting essentially of the amino acid sequence of *B. stearothermophilus* lactate dehydrogenase and being characterised by having a higher catalytic activity for for homologues of lactic acid of formula $C_nH_{2n+1}CHOHCOOH$ wherein n is $>1$ as substrate than for lactate.

Such recombinant thermophilic NAD-dependent dehydrogenases preferably consist of at least 75% of the amino acids of *B. stearothermophilus* lactate dehydrogenase. Most preferably, they consist essentially of the amino acid sequence of *B. stearothermophilus* lactate dehydrogenase. By "consisting essentially of the amino acid sequence of *B. stearothermophilus* lactate dehydrogenase" is meant having major sequence homology at the amino acid level, for example having at least 75% of the amino acids of *B. stearothermophilus* lactate dehydrogenase. (See attached Figure, from ref 1). Normally, the sequence homology should be at least 904 and suitably should be at least 98%.

The invention further provides method of producing a recombinant thermophilic NAD-dependent dehydrogenase having a selected substrate specifity, which comprises modifying a cloned DNA sequence coding for an NAD-dependent dehydrogenase so as to form a modified DNA sequence coding for a modified NAD-dependent dehydrogenase having a higher catalytic activity for for homologues of lactic acid of formula $C_nH_{2n+1}CHOHCOOH$ wherein n is $>1$ as substrate than for lactate, and expressing the modified NAD-dependent dehydrogenase in a host.

As indicated, the modified DNA sequence may code for an enzyme having a hydrophobic amino acid residue at at least one of positions 102 and 104 and/or having in the region extending from positions to 237 at least one amino acid capable of destabilising α-helices.

Most preferably the modifications result in the production of modified DNA sequences which, on expression, code for enzymes having the preferred amino acid sequences referred to above.

The cloned DNA sequences may be modified by any conventional technique, for example by site-directed mutagenesis.

Using the techniques described herein we have constructed a novel dehydrogenase from a lactate dehydrogenase framework by changing one or more amino acids on the mobile coenzyme-loop (residues 98–110).

In carrying out the invention, we utilised the DNA which encodes the protein polypeptide chain for lactate dehydrogenases from the thermophilic bacteria, *B. stearothermophilus*. The nucleotide sequences of the genes were determined and the DNA, together with regions of sequence both up and downstream of the gene were used to transfect *E. coli*. The *E. coli* construction overexpressed lactate dehydrogenase with amino acid sequence, thermal stability and enzyme catalytic properties which were identical to the same enzyme when expressed by the parent thermophilic organism (Refs 1 and 2).

The technique of site-directed mutagenesis, as described in Reference 3 was used to specifically alter the amino acid sequence of the original wild-type lactate dehydrogenase enzyme to obtain proteins with new amino acid sequences.

As indicated, the procedure used to produce our novel constructs was olignucleotide directed mutagenesis. This technique enabled us to produce and isolate in large quantities, enzyme proteins with both single and multiple variations on the original lactate dehydrogenase amino acid sequence.

The procedures employed were as follows:

Mutations were introduced into the LDH gene from *B. stearothermophilus* using the oligonucleotide mismatch procedure in M13 with the mutagenic oligonucleotide as the primer for in vitro chain extensions, To accommodate hydrophobic a-karo acids larger than pyruvate, amino acid substitutions have been made to increase the flexibility of a helix which borders the active site (mutations $^{235\text{-}6}AA\rightarrow GG$) and to introduce hydrophobic residues into the substrate binding site (mutations $^{102\text{-}5}QKP\rightarrow MVS$). The two sets of mutations were made on separate genes. In order to obtain a construction with both sets of changes, these two mutant genes were restricted at sites between the two areas changed and the two fractions containing the mutations were ligated together.

The sequences of the oligonucleotides used to make the mutations were as follows ("WT"-wild type):

```
102-5
    QKP─→MVS
                              * * * * * * *
    OLIGONUCLEOTIDE    3'CCGCGGTTGTACCACAGCCCGCTCTGC5'
    WT                 5'—GGCGCCAACCAAAAACCGGGCGTGACG—3'

235-6AA─→GG
                              *  *
    OLIGONUCLEOTIDE    3'CGCGCTACCGCCGATGGTTTA5'
    WT                 5'—GCGCGATGCCGCCTACCAAAT—3'
```

The mutant genes were expressed in *E. Coli* TG2 cells in the vector pKK223-3 and the protein purified to homogeneity by chromatography on Blue Sepharose (F3GA) and Q-Sepharose Fast Flow. The level of expression of these routants was 25–30% of the soluble *E. coli* protein.

Steady-state reaction rates were determined by following the change in $A_{340}$ due to the consumption of NADH. Thermal stability measurements were made at pH 6 over a range of temperatures. The concentration of protein in the incubations was 2 μM (subunits) and samples were incubated at each temperature for 20 minutes and stored on ice prior to assay. The buffer for all experiments was 100rmM triethanolamine-HCl/NaOH, pH 6.

RESULTS

The steady-state catalytic properties of the wild-type and the mutant enzymes, shown in Table 2, demonstrate that the mutations have altered the specificity of lactate dehydrogenase, producing α-hydroxy acid dehydrogenases with broader substrate specificity. The mutant enzymes are better able to tolerate substrates with bulky side chains than the wild type enzyme does.

The mutant enzyme containing $^{102\text{-}5}QKP\rightarrow(MVS)$, catalyses the reduction of the various substrates at rates (as measured by $k_{cat}$) similar to those catalysed by the wild-type enzyme, but has a higher $K_m$ for pyruvate and a lower $K_m$ for all the larger aliphatic substrates than the parent enzyme. The mutant enzyme containing $^{235\text{-}6}AA\rightarrow(GG)$ has a relatively high $K_m$ for all of the substrates tested (compared with the wild-type enzyme) but the $k_{cat}$ is greater than that for the parent enzyme for all substrates larger than α-ketovalerate. The combination of both sets of mutation in the MVS/GG mutant gives rise to an α-hydroxy acid dehydrogenase which is largely non-specific for a range of substrates. This mutant enzyme has a higher specific activity (as measured by $k_{cat}/K_m$) than the wild-type enzyme for all the substrates that are shown here which have side chains larger than that of pyruvate.

Several lines of evidence indicate that the mutations have not had widespread structural consequences in the protein molecule. The mutant enzymes are still allosterically controlled by fructose-1,6-bisphosphate (FBP). The activity of the wild-type enzyme shows a stimulation in $k_{cat}/K_m$ of 50-fold in the presence of 5mM FBP, whilst the stimulations of the activities of the mutant enzymes are 100-fold for MVS, 60-fold for GG and 16-fold for MVS/GG when assayed with pyruvate. The binding properties of NADH have not been adversely affected by the mutations. Steady state kinetics in the presence of 0.5 mM pyruvate show that the $K_m$ for NADH binding is 18 µM for the wild-type and GG enzymes and 14.5 µM for the MVS and MVS/GG enzymes. The mutant enzymes still retain high thermal stability. The results presented in graphical for in FIG. 2 deonstrate that the temperature at which activity falls to 50% of its original value after a 20 minute incubation is the same for the MVS mutant protein as that of the wild-type enzyme (77° C.), whilst that for the GG and MVS/GG enzymes has fallen slightly to 72° C. However, all of the enzymes are 100% active at 60° C., indicating that they retain thermal stability from the parent enzyme.

with the substitution of hydrophobic residues into a loop of polypeptide which closes over the active site after the substrate has bound (Met, Val and Set replace Gln, Lys and Pro at 102-5) enables the enzyme to accommodate larger aliphatic side chains than that which is naturally preferred ($CH_3$).

Thus the effect of introducing the two glycine residues into helix-G would be to increase its flexibility and allow larger molecules to have access to the active site.

An explanation for the observation that the $k_{cat}$ for larger substrates is improved may be that they are able to bind in more favourable orientations for effective catalysis although the $K_m$ is unaffected. The introduction of methionine and valine into the loop instead of glutsmine and lysine will have made this region of the protein more hydrophobic, so that substrates with aliphatic side chains will be able to bind to the protein more easily (giving rise to the improved $K_m$s observed) The proline to serine mutation may give the loop more

TABLE 2

Steady-state properties of the mutant and wild-type enzymes.

| Substrate | | WT | MVS | GG | MVS/GG |
|---|---|---|---|---|---|
| Pyruvate + | $k_{cat}$ (s$^{-1}$) | 250 | 66 | 167 | 32 |
| 5 mM FBP | $K_M$ (mM) | 0.06 | 0.16 | 4 | 4 |
| | $k_{cat}/K_M$ (M$^{-1}$s$^{-1}$) | $1.4 \times 10^6$ | $4.1 \times 10^5$ | $4.2 \times 10^4$ | $3 \times 10^3$ |
| α-KB + | $k_{cat}$ (s$^{-1}$) | 186 | 31 | 92 | 205 |
| 5 mM FBP | $K_M$ (mM) | 1.1 | 0.17 | 2.9 | 3.3 |
| | $k_{cat}/K_M$ (M$^{-1}$s$^{-1}$) | $6.4 \times 10^5$ | $1.8 \times 10^5$ | $3.2 \times 10^4$ | $6.2 \times 10^4$ |
| α-KV + | $k_{cat}$ (s$^{-1}$) | 51 | 9.5 | 58 | 166 |
| 5 mM FBP | $K_M$ (mM) | 8 | 1 | 8.3 | 4 |
| | $k_{cat}/K_M$ (M$^{-1}$s$^{-1}$) | $6.4 \times 10^3$ | $9.5 \times 10^3$ | $7.0 \times 10^3$ | $4.2 \times 10^4$ |
| α-KC + | $k_{cat}$ (s$^{-1}$) | 29 | 20 | 240 | 185 |
| 5 mM FBP | $K_M$ (mM) | 3.4 | 2.3 | 5.6 | 7.1 |
| | $k_{cat}/K_M$ (m$^{-1}$s$^{-1}$) | $8.5 \times 10^3$ | $8.7 \times 10^3$ | $4.3 \times 10^4$ | $2.6 \times 10^4$ |
| α-KIV + | $k_{cat}$ (s$^{-1}$) | 0.26 | 0.55 | 0.68 | 11.3 |
| 5 mM FBP | $K_M$ (mM) | 22 | 8.2 | 14.3 | 22 |
| | $k_{cat}/K_M$ (M$^{-1}$s$^{-1}$) | 12 | 67 | 50 | 570 |
| α-KIC + | $k_{cat}$ (s$^{-1}$) | 0.33 | 0.67 | 1.74 | 18.5 |
| 5 mM FBP | $K_M$ (mM) | 6.7 | 1.9 | 15.4 | 14.3 |
| | $k_{cat}/K_M$ (M$^{-1}$s$^{-1}$) | 50 | 353 | 110 | $1.3 \times 10^3$ |
| Pyruvate | $k_{cat}$ (s$^{-1}$) | 250 | 61 | | |
| No FBP | $K_M$ (mM) | 3.0 | 15 | >50 | >50 |
| | $k_{cat}/K_M$ (M$^{-1}$s$^{-1}$) | $8.3 \times 10^4$ | $4.1 \times 10^3$ | 665 | 190 |

WT = wild-type enzyme
MVS = enzyme containing the $^{102-5}$QKP → MVS substitution
GG = enzyme containing the $^{235-6}$AA → GG substitution
MVS/GG = enzyme containing $^{102-5}$QKP → MVS and $^{235-6}$AA → GG substitutions
α-KB = α-Ketobutyrate, $CH_3CH_2COCOO^-$
α-KV = α-Ketovalerate, $CH_3(CH_2)_2COCOO^-$
α-KC = α-Ketocaproate, $CH_3(CH_2)_3COCOO^-$
α-KIV = α-Ketoisovalerate, $(CH_3)_2CHCOCOO^-$
α-KIC = α-Ketoisocaproate, $(CH_3)_2CHCH_2COCOO^-$

DISCUSSION

The results presented herein have demonstrated that we have succeeded in redesigning the active site of lactate dehydrogenase so that it will recognise and turnover a range of aliphatic α-keto acids, while maintaining the redox chemistry of the enzyme.

Previous studies have shown the catalytic importance of several residues in the active site; His-195 donates a proton to the substrate, Asp-168 stabilises the protonated form of His-195 in the ternary complex, Arg-109 polarises the substrate carbonyl bond during the transition state and ARE-171 forms a very tight bond with the substrate carboxylate and orients the substrate for effective catalysis.

Although not wishing to be limited by theory, it is believed that the effects of the mutations which have been made are as follows:

The replacement of two alenine residues at positions 235-6 by glycines is believed to increase the flexibility of helix-G which borders the active site. This, together segmental flexibility and so allow larger substrates to access the active site of the enzyme.

It is an advantage for the use of enzymes in the synthesis of organic compounds if the enzymes will transform as wide a range of compounds as possible, while retaining the property of yielding 100% entantiomeric excess of product at the carbon atom which is reduced. In this invention we have constructed side chain binding pockets which will accommodate a very wide range of substrate side-chains by creating a localized pool of mobile hydrophobic amino acids side chains. That is we have designed and made inside a protein an environment akin to 'hot organic solvent' which will be able to easily dissolve a wide range of differently sized substituted pyruvates. The solvent was provided by the mutations to give MVS, mainly hydrophobic side chains. The 'heat' was generated by inserting into a stable helix two glycine residues which destabiliz the helix and thus give rise to more rapid local atomic motion i.e. to heat.

REFERENCES (1) Cloning. expression and complete nucleotide sequence of the
*Bacillus stearothermophilus* L-lactate dehydrogenase gene.
Barstow D; Clarke A R; Chia W N; Wigley D; Sherman A F; Atkinson T;
Minton N P; Holbrook J J
Gene (1986)46 47–55

(2) Amino acid sequence of the L-lactate dehydrogenase og *Bacillus caldotenax* deduced from the nucleotide sequence of the cloned gene
Barstow D; Murphy J P; Sherman A F; Clarke A R; Holbrook J J;
Atkinson T;
Eur. J. Blochem. (1987) 185 581–6

(3) Site-directed mutagenesis reveals the role of a mobile arginine residue in lactate dehydrogenase catalysis.
Clarke A R; Wigley D B; Chia W N; Barstow D; Atkinson T;
Holbrook J J;
Nature (1986) 324 699–702

(4) $k_{cat}125s^{-1}$ for a *B. stearothermophilus* malate dehydrogenases
on a different protein framework isolated in 1967
Murphey W H; Barnaby C; Lin F J; Kaplan N O; (1967)
J. Biol. Chem. 242 1548–59)

We claim:

1. A recombinant thermophilic NAD-dependant dehydrogenase consisting essentially of the amino acid sequence depicted in FIG. 1, and having the mutation 102-5 GlnLysPro→MetValSer.

2. A recombinant thermophilic NAD-dependent dehydrogenase consisting essentially of the amino acid sequence depicted in FIG. 2, and having the mutation of 102-5 GlnLvsPro→MetValSer and 235-6 AlaAla→GlyGly.

* * * * *